(12) United States Patent
Nuckols et al.

(10) Patent No.: US 6,463,925 B2
(45) Date of Patent: Oct. 15, 2002

(54) HOT WATER HEATER FOR DIVER USING HYDROGEN CATALYTIC REACTIONS

(75) Inventors: Marshall L. Nuckols, Annapolis, MD (US); Kirk Van Zandt, Panama City, FL (US); W. Scott Finlayson, Annapolis, MD (US); Kenneth Price, Lynn Haven, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/770,741

(22) Filed: Jan. 24, 2001

(65) Prior Publication Data

US 2001/0018915 A1 Sep. 6, 2001

Related U.S. Application Data

(63) Continuation-in-part of application No. 09/448,405, filed on Nov. 22, 1999.

(51) Int. Cl.[7] .............................................. B63C 11/28
(52) U.S. Cl. .................................. 126/208; 128/204.17
(58) Field of Search ................................. 126/204, 209, 126/210, 208; 122/4 D; 128/204.17

(56) References Cited

U.S. PATENT DOCUMENTS

| | | | | |
|---|---|---|---|---|
| 2,983,259 A | * | 5/1961 | Wittke | 122/4 D |
| 3,385,286 A | * | 5/1968 | Jones | 126/204 |
| 4,195,619 A | * | 4/1980 | Hollen | 126/204 |
| 5,476,375 A | * | 12/1995 | Khinkis et al. | 122/4 D |
| 6,167,846 B1 | * | 1/2001 | Ogino et al. | 122/4 D |

* cited by examiner

Primary Examiner—Sara Clarke
(74) Attorney, Agent, or Firm—Harvey A. Gilbert; Donald G. Peck

(57) ABSTRACT

A catalytic heater supplies heated water that circulates to heat a diver's suit. An insulating housing closed at opposite ends by cap members defines a chamber containing a catalyst inside of a multi-tube heat exchanger. Fittings in the cap members pass water through the multi-tube heat exchanger to and from the suit, and a gas circuit flows mixed hydrogen and oxygen to the catalyst that reacts with the mixed hydrogen and oxygen to produce heat that heats the water in the multi-tube heat exchanger for the diving suit. Optionally, hydrogen may be mixed with oxygen from a breathing gas mixture so that after heating the water, the gases remaining may be breathed by the diver. The catalytic heater provides a safe, reliable source of warm water for active thermal protection of divers over a wide range of diving applications. The heater can be used in an open, closed or semi-closed configuration to support surface tethered diving applications or autonomous, self-contained missions with free-swimming divers or within wet or dry underwater vehicles. Water temperatures can be easily adjusted when using this heater by regulating the percentage of hydrogen injected into the bed of catalyst. The catalytic heater can be used either as the primary active heating source or as a backup heating system in the event failure occurs to the primary heat source.

15 Claims, 2 Drawing Sheets

HOT WATER HEATER FOR DIVER USING HYDROGEN CATALYTIC REACTIONS

CROSS REFERENCE TO RELATED APPLICATION

This is a continuation-in-part of copending U.S. patent application entitled "Method and System for Heating and Humidifying a Breathable Gas" by M. L. Nuckols et al., U.S. Patent and Trademark Office Ser. No. 09/448,405 (N.C. 79938), filed Nov. 22, 1999 and incorporates all references and information thereof by reference herein.

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION

(1) Field of the Invention

The present-invention relates generally to heaters for diving suits. More particularly, this invention relates to a portable catalytic heater relying on catalytic combustion of hydrogen to heat circulating water for a diving suit.

(2) Description of the Prior Art

The necessity for providing heat for both active and inactive divers during long duration, cold-water operations in swimmer delivery vehicles is well established. One documentation in support of this need is presented by M. W. Nuckols et al. in their article "Active Diver Thermal Protection Requirement for Cold Water Diving" *J. Aviation, Space and Environmental Medicine*, Vol. 54, No. 7 pp 644–648 (1983). Alternative approaches to supply this requirement for active heating have covered a wide range of technologies, including thermoelectric heaters, heaters using magnesium combustion such as the heater referred to as the Conox, propane/catalytic heating, and heating by direct electrical resistive means. While all of these methods have been shown to be capable of producing sufficient quantities of heat, each has its own inherent restrictions and interface issues when applied to diving operations involving swimmer delivery vehicles. Most prominent of these issues are the requirements of consumption of power for a heater that compete and detract from the power requirements for propulsion of the swimmer delivery vehicle. Another prominent issue is the requirement for packaging the heater for environments that are limited in space.

Thus, in accordance with this inventive concept, a need has been recognized in the state of the art for a heater for a diving suit that provides a safe, reliable source of warm water for active thermal protection of divers over a wide range of diving applications.

SUMMARY OF THE INVENTION

One form of a catalytic heater has an insulating housing closed at opposite ends by cap members to define a chamber containing a catalyst inside of a multi-tube heat exchanger. Fittings in the cap members pass circulating water through the multi-tube heat exchanger to and from a diver's suit, and a gas circuit flows mixed hydrogen and oxygen to the catalyst that reacts with the mixed hydrogen and oxygen to produce heat that heats the water in the multi-tube heat exchanger for the diving suit.

An object of the invention is to provide a compact heater to provide heated water for a diving suit.

Another object of the invention is to provide a safe, reliable source of warm water for active thermal protection of divers over a wide range of diving applications.

Another object of the invention is to provide a catalytic heater capable of being used in open, closed or semi-closed circuit configurations to support tethered diving applications, autonomous self-contained applications by free-swimming divers, or life support systems within wet or dry underwater swimmer delivery vehicles.

Another object of the invention is to provide a catalytic heater providing adjustment of temperature of circulating heated water by regulating the percentage of hydrogen injected into its catalyst bed.

Another object of the invention is to provide a compact catalytic heater that can be used either as the primary active heating source or as a backup heating system if failure occurs in the primary heat source.

Another object of the invention is to provide a catalytic heater that facilitates reaction of hydrogen with a small amount of oxygen in a gas mixture to produce heat transferred through a multi-tube heat exchanger to a circulating liquid that carries this heat to the diver.

Another object of the invention is to provide a catalytic heater having rates of production of heat that can be increased while using the same gas mixture by operating at elevated pressures.

Another object of the invention is to provide a catalytic heater having rates of production of heat increased by using carrier gases other than air, such as using a helium and oxygen gas mixture.

Another object of the invention is to provide a catalytic heater recirculating the gas mixture used to heat circulating water to increase efficiency.

Another object of the invention is to provide a catalytic heater having its heating capacity easily controlled with a simple mechanical metering valve for the hydrogen.

Another object of the invention is to provide a catalytic heater that does not require an active heating source.

Another object of the invention is to provide a catalytic heater that continues to provide heating of the whole body as long as hydrogen is present in the gas mixture.

Another object of the invention is to provide a catalytic heater that provides water vapor as a by-product of the reaction to possible help humidify breathing gases.

Another object of the invention is to provide a catalytic heater controlling water temperatures by simply adjusting the percentage of hydrogen passing through the catalyst bed.

Another object of the invention is to provide a catalytic heater having operational costs that are a fraction of the cost of batteries used in conventional electrical resistive heating systems.

These and other objects of the invention will become more readily apparent from the ensuing specification when taken in conjunction with the appended claims.

DESCRIPTION OF THE PREFERRED EMBODIMENTS

Figure 1:
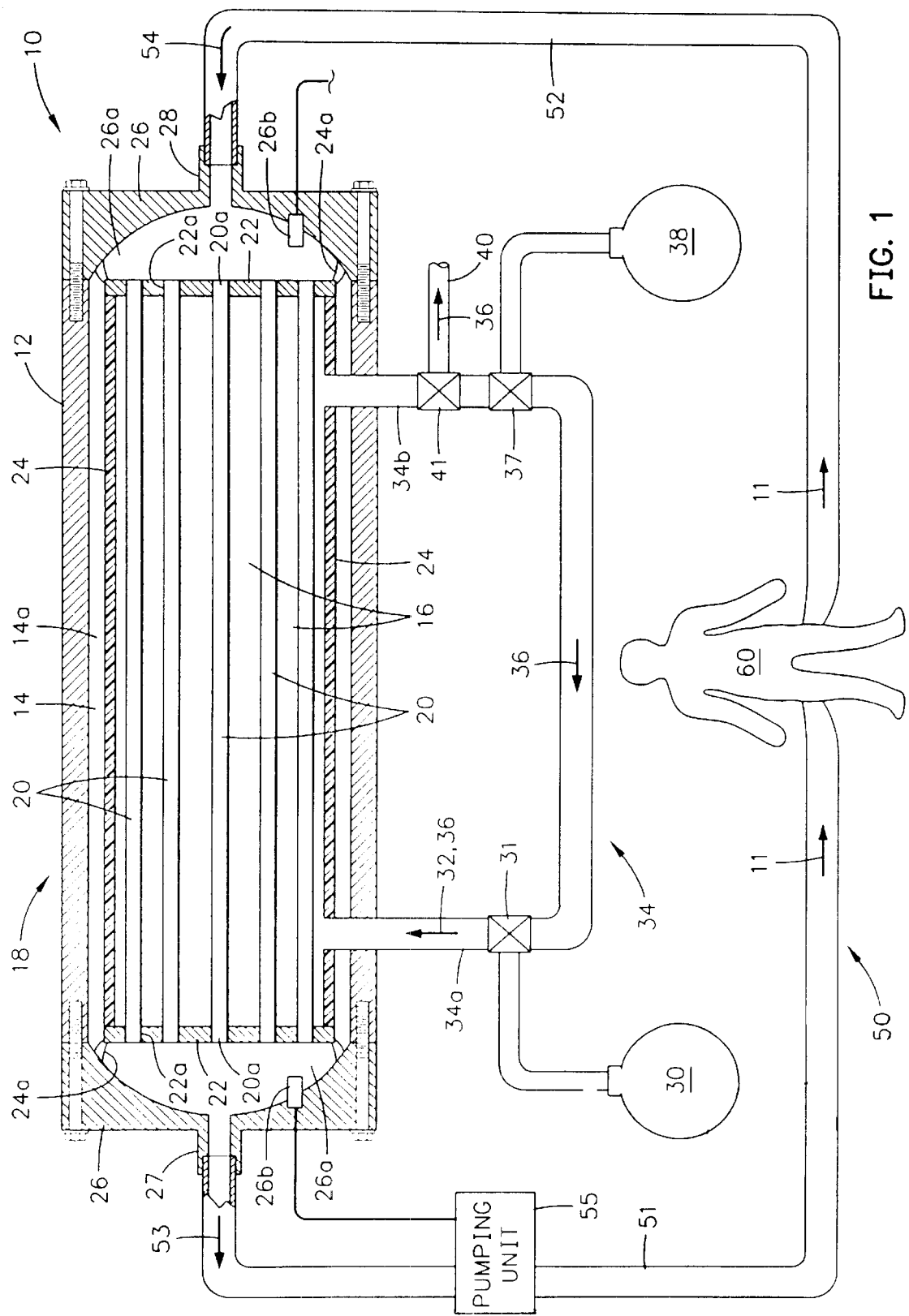
FIG. 1 is a schematic longitudinal cross-sectional view of one form of the catalytic heater of this invention connected to supply heated water to a diver. Another form can have the catalyst bed up stream of the catalyst bed.

Referring to FIG. 1 and in accordance with this invention, testing of a simple hydrogen catalytic combustion heater for use as a breath heater for deep diving applications (referenced above), led to the discovery that the concept of this heater might be adapted and modified to heat a diver's suit. The testing of the breath heater is documented in M. L. Nuckols, et al.'s article "Design and Evaluation of a Hydrogen Catalytic Breath Heater For Diving Applications", *Proc. of Underwater Intervention* 2000, Houston, Tex. January 2000. According to this invention, the concept of high heat demonstrated during this testing has been advantageously developed in catalytic heater 10 for a diver to potentially minimize package size and power requirements and yet meet all the heating requirements for providing sufficient heat underwater for a diver during missions of long duration. The hydrogen catalytic combustion heater previously tested for only heating a diver's breath consisted of a canister filled with a chemical catalyst located just upstream from the divers helmet or gas supply regulator. A number of candidates for the catalyst were tested including precious metals such as platinum or palladium deposited on a support matrix of porous carbon or alumina particles in a catalyst bed. A small percentage of hydrogen was injected into the breathing gas mixture prior to passing it through the catalyst bed. As the gas mixture flowed through the canister the catalyst facilitated the reaction of hydrogen with a small amount of oxygen (½ mol of oxygen is consumed for every mol of hydrogen that is reacted) in the breathing gas mixture to produce water vapor and approximately 104,000 Btu's (110,000 kJ) of heat according to the chemical reaction:

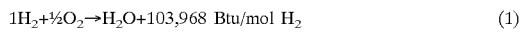

$$1H_2 + \tfrac{1}{2}O_2 \rightarrow H_2O + 103{,}968 \text{ Btu/mol } H_2 \tag{1}$$

This heater not only warmed the breathing gas just before the diver inhaled it but also added water vapor to humidify the breathing gas.

Catalytic heater 10 of water in accordance with this invention uses such catalytic combustion of hydrogen to heat liquid 11, usually water, that is coupled to a hose 50 arranged to provide a loop for circulating water 11 to and from a diving suit 60. Hose loop 50 includes a pair of hose sections 51 and 52 that are connected to diving suit 60 and catalytic heater 10 to supply heated water 53 to suit 60 via hose section 51 and receives cooled water 54 from suit 60 via hose section 52 for reheating. One or more pumping units 55 can be interposed in one or both of hose sections 51 and 52 (only one pumping unit 55 is shown) and can include suitable preprogrammed control circuitry and equipment, such as flow sensors and valves to selectively change flow rate if desired, and pumping unit 55 also can be coupled to suitable temperature sensors in the hoses and/or suit to assure that the right amounts of water 11 are heated to the right temperatures and being circulated in hose loop 50. Catalytic heater 10 and pumping unit 55 can be made compact to be carried by the diver in a pack, or they may larger and located in a nearby work station or swimmer delivery vehicle and connected to the diver via longer versions of hose sections 51 and 52.

Catalytic heater 10 has insulating jacket 12 functioning as an elongate housing that contains an insulated chamber 14 that is filled with chemical catalyst 16 and a manifold-like, multitube heat exchanger 18. Optionally, jacket 12 could be formed as a shell-like canister having a separate insulating layer inside of it, for example.

Multi-tube heat exchanger 18 has a plurality of elongate hollow metal tubes 20 having openings 20a at opposite ends aligned and joined with a like number of openings 22a in disc-shaped end members 22, and tubes 20 are secured and sealed at their opposite ends to disc-shaped end members 22. Multi-tube heat exchanger 18 also has a cylindrical shell-like casing 24 extending between and secured and sealed to the peripheries of both disc-shaped end members 22. Tubes 20, end members 22 and casing 24 are preferably made of compatible and strong, heat-conductive metals, although other materials having the same properties could be used. An annular passageway 14a in chamber 14 is created between the outer surface of casing 24 and the inner surface of jacket 12.

Chemical catalyst 16 substantially fills the spaces inside of casing 24 and end members 22 and between and around tubes 20 of multi-tube heat exchanger 18. Chemical catalyst 16 may be selected from a number of potential candidates and may include precious metals such as platinum or palladium deposited in a bed on a support matrix of porous carbon or alumina particles. One of the more promising candidates that showed the best results for chemical catalyst 16 was made up of extruded pellets of 0.8% palladium on carbon.

Cap members 26 are secured and sealed to jacket 12 by bolts, for example, and disc-shaped end members 24 are held in place with spacer elements 24a to help define annular passageway 14a in chamber 14. Cap members 26 each have a recess 26a to permit fluid communication with openings 20a of tubes 20 and annular passageway 14a. Outlet and inlet fittings 27 and 28 extend from cap members 26 from jacket 12 and are connected to hose section 51 and hose section 52, respectively. Cap members 26 are fabricated from a rugged and insulating material, such as polyethylene, and may each have one or more thermocouples 26b in recess 26a that extend to remote monitoring equipment and/or pumping unit 55 to indicate temperatures of flows of water 53 and 54. Water 54 flowing through fitting 28 and into recess 26a passes in part to tubes 20 and in part to annular passageway 14a for heating by catalyst 16. The parts of heated water are collected from tubes 20 and annular passageway 14a in recess 26a and passed through fitting 27.

Catalytic heater 10 has a source, or tank of hydrogen 30 coupled to valve 31 to inject hydrogen 32 into a semi-closed gas loop circuit 34 and to the spaces inside multi-tube heat exchanger 18 of catalytic heater 10 via an inlet portion 34a of gas circuit 34. Breathing gas mixture 36 containing some oxygen from source, or tank of breathing gas 38 is injected through gas injector valve 37 and is injected into gas circuit 34. Injected breathing gas mixture 36 is mixed with hydrogen 32 down-stream of valve 31 in gas circuit 34, and then the mixed hydrogen 32 and oxygen of breathing gas 36 are fed into chamber 14 of catalytic heater 10 via inlet portion 34a of gas circuit 34. Valves 31 and 37 in gas circuit 34 not only assure that the flow of gases in gas circuit goes to and from catalyst 16 of catalytic heater 10, but also that the hydrogen and oxygen are suitably mixed to produce the catalytic reaction with catalyst 16. Both valves 31 and 37 are manually controlled, or may be automatically controlled, or adjusted to control temperatures of water 53 by regulating the percentage of hydrogen injected into the bed of catalyst 16. Compared to breathing gas mixture 36, the percentage of hydrogen 32 injected is relatively small, as will be explained below. Mixed hydrogen 32 and breathing gas mixture 36 circulate through chemical catalyst 16 in the spaces around tubes 20 of multi-tube heat exchanger 18 where at least parts of the mixture react with catalyst 16 and produce heat.

Parts of breathing gas mixture 36 and hydrogen 32 not converted to heat pass through chemical catalyst 16 in spaces in multi-tube heat exchanger 18 in heater 10 and into an outlet portion 34b of gas loop circuit 34. A small portion of the gas loop circuit 34, which has been warmed and at least partially humidified in heater 10 may be passed to feeder line 40 via valve 41 to be breathed by the diver in a semi-closed gas loop circuit, or other breathing gas supply system, or dumped overboard. The major portion of the gas loop circuit 34 passes through valve 41 to be recirculated for mixing with additional hydrogen 32 from source 30 and gases from source 38 to further react with catalyst 16 to produce more heat. Alternatively to using semi-closed gas loop circuit 34, pre-mixed flows of breathing gas 36 could include air, nitrox or heliox mixtures with a small percentage of hydrogen 32 and could be supplied to heater 10 via inlet portion 34a and vented from heater 10 via outlet portion 34b in an open circuit configuration.

As gas mixture 36 and hydrogen 32 flow through heater 10, chemical catalyst 16 facilitates the reaction of hydrogen 32 with a small amount of oxygen in gas mixture 36 to produce heat and water vapor. About ½ mol of oxygen in gas mixture 36 is consumed for every mol of hydrogen 32 that is reacted. Most of this heat is transferred to heat cooler water 54 from diving suit 60 as it passes through hollow tubes 20 of heat exchanger 18. Circulating hose 50 carries this heat back to diver's suit 60 in the form of heated water 53. The remainder of this heat and the water vapor by-product respectively heats and humidifies the remainder of the breathing gas that is vented through feeder line 40 to the diver's breathing system if it is desired to use this portion of the breathing gas in this way. If all of the heat transferred from reacting catalyst 16 went into heating up water 54 as it passed through tubes 20 and annular passageway 14a adjacent the bed of chemical catalyst 16, the theoretical temperature rise across the chemical catalyst 16 due to the complete combustion of hydrogen can be calculated as:

$$\Delta T = \frac{\dot{Q}}{\dot{V}_{mix} \rho_{mix} C_{P_{mix}}} \quad (2)$$

where $\dot{Q}$ is the heat rate produced by the hydrogen combustion, Btu/min; $\dot{V}_{mix}$ is the volumetric flow rate of the gas mix through the bed, ft³/min; $\rho_{mix}$ and $C_{\rho mix}$ are the density and specific heats of the gas mixture, respectively. The heat production rate can be found by multiplying the molar flow rate of hydrogen, $\dot{N}_{H_2}$, by its heat of reaction (103,968 Btu/mol), or:

$$\dot{Q} = \dot{N}_{H_2} \cdot 103{,}968 \; \frac{\text{Btu}}{\text{mol H}_2} \quad (3)$$

The hydrogen molar flow rate can be found by dividing the total flow rate of the gas mixture, $\dot{m}_{mix}$, by the mass of gas mixture per mol of hydrogen, or $$\dot{N}_{H_2} = \frac{\dot{m}_{mix}}{\frac{m_{mix}}{\text{mol H}_2}} = \frac{\rho_{mix} \dot{V}_{mix}}{\frac{m_{mix}}{\text{mol H}_2}} \quad (4)$$

Substituting equations (3) and (4) into equation (2) gives $$\Delta T = \frac{\frac{\rho_{mix} \dot{V}_{mix}}{\frac{m_{mix}}{\text{mol H}_2}} \cdot 103{,}968}{\dot{V}_{mix} \rho_{mix} C_{P_{mix}}} = \frac{103{,}968}{C_{P_{mix}} \frac{m_{mix}}{\text{mol H}_2}} \quad (5)$$

For example, when air mixed with 1% hydrogen is passed over the catalyst bed of chemical catalyst 18 at sealevel (1 standard atmosphere) conditions, it has the following gas properties and theoretical temperature rise when the hydrogen combusts stochiometrically:

$$C_{Pmix} = 0.245 \; \frac{\text{Btu}}{\text{lbm} - {}^\circ \text{F}};$$

$$\frac{m_{mix}}{\text{mol H}_2} = 2854 \; \frac{\text{lbm mix}}{\text{mol H}_2};$$

$$\Delta T = 148.4^\circ \text{ F}.$$

Figure 2:
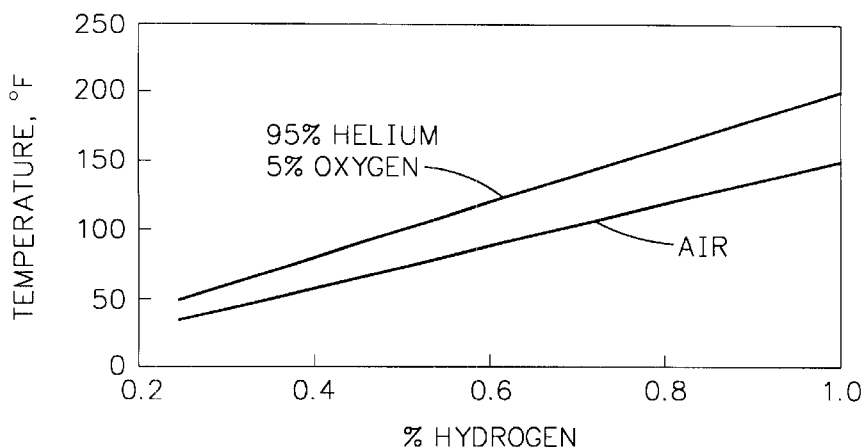
FIG. 2 shows the effect of hydrogen percentage on theoretical temperature of the gas.

Referring to FIG. 2, by simply varying the percentage of hydrogen 32 present in gas mixture 36, the theoretical temperature rise across the catalyst bed of chemical catalyst 16 can be controlled. Actuating valves 31 and 37 to increase the percentage of hydrogen 32 with respect to gas mixture 36 increases the production of heat in catalyst 16, and decreasing the percentage of hydrogen 32 with respect to gas mixture 36 decreases the production of heat in catalyst 16. Increasing and decreasing the pressure in the catalytic heater 10 might create the same effect. In addition, these theoretical temperature rises can be increased somewhat by using carrier gases other than air, for example by using the helium and oxygen mixture shown. These higher temperatures created at the same volume fraction of hydrogen 32 are a result of the lower mass of helium per mole of hydrogen when compared to air. Actual temperature rises in catalyst 16 would be expected to be somewhat lower than these theoretical values since much of the heat generated in the catalyst bed of chemical catalyst 16 will be transferred through heat exchanger 18 into water 53 and 54 circulating to and from suit 60.

Figure 3:
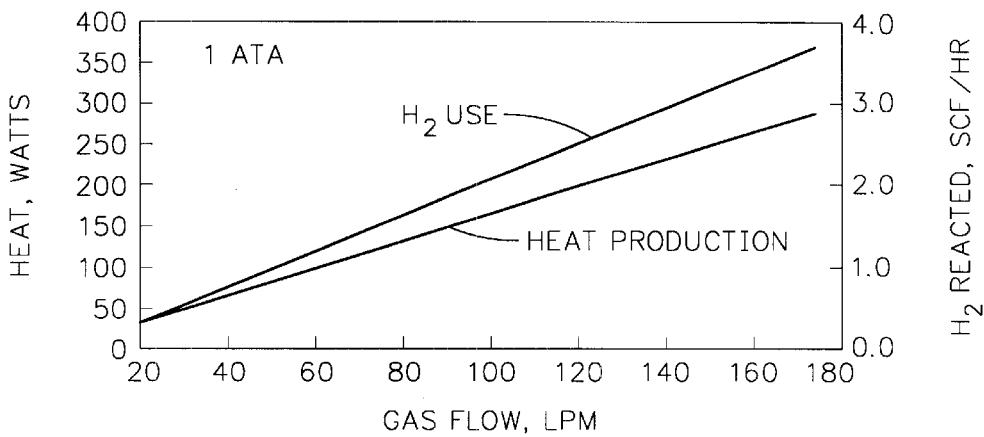
FIG. 3 shows the heat production rates and hydrogen combustion rates of the hydrogen catalytic water heater of the invention with 1% hydrogen in air at standard atmospheric pressure at the surface.

FIG. 3 shows the amount of heat that will be released by the combustion of 1% hydrogen in an air breathing mixture 36 at different flow rates of air, and the amount of hydrogen combusted if the catalyst bed is at standard atmospheric pressure. Actuating valves 31 and 37 to increase the flow rate of hydrogen 32 and gas mixture 36 increases production of heat in catalyst 16, and decreasing the flow rate of hydrogen 32 and gas mixture 36 decreases production of heat in catalyst 16. Increasing and decreasing the pressure in catalytic heater 10 might create the same effect. A flow rate of air of approximately 170 liter-min$^{-1}$ (6 ft³/min) through catalytic heater 10 will consume 3.6 standard cubic feet (SCF) of hydrogen per hour and generate approximately 280 watts of heat.

Figure 4:
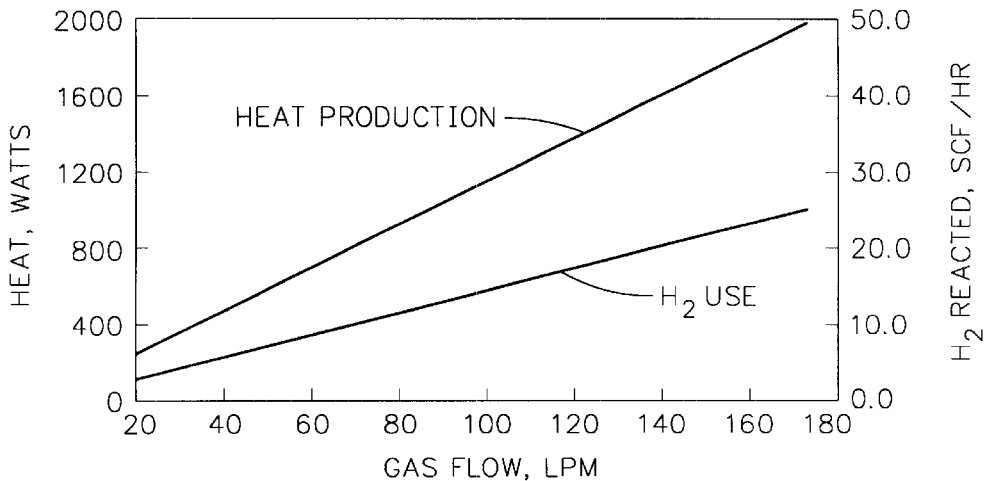
FIG. 4 shows heat production rates and hydrogen combustion rates with 1% hydrogen in air when operating the catalyst heater at 100 psi.

Referring to FIG. 4, the heat production rates can be increased while using the same gas mixture by operating catalytic heater 10 at elevated pressures. Valves 31 coupled to hydrogen source 30 and valve 37 coupled to the source 38 of oxygen and other gases 36 (which may be air, although other more sophisticated breathing mixtures may be selected) are appropriately actuated to increase the pressure, or to create elevated pressures in gas circuit 34 and catalyst 16 inside multi-tube heat exchanger 18. These elevated pressures have been found to increase the production of heat in catalyst 16. Under these conditions at an air flow rate of about 170 liter-min$^{-1}$ (6 ft$^3$/min), catalytic heater 10 will consume approximately 24 standard cubic feet (SCF) of hydrogen per hour and generate nearly 2 kilowatts of heat.

Realistic heating levels could be obtained when using hydrogen catalytic combustion heater 10 of the invention as an active thermal protection system for divers. Approximately 0.5 kg of chemical catalyst 16 consisting of 0.8% palladium deposited on extruded carbon pellets was added to the spaces around hollow tubes 20 inside casing 24 of multi-tube heat exchanger 18. The pellets of chemical catalyst 16 were packed around the stainless steel tubing of tubes 20 running through the center core of the heat exchanger 20. During testing, parts of water 54 passed through tubes 20, as well as parts of water 54 passed through annular passageway 14a between multi-tube heat exchanger 18 and polyethylene outer jacket 12 at a rate of 0.2 gallons per minute. A steady flow of 1% hydrogen 32 mixed in a breathing mixture of air 36 from source 38 passed through catalyst 16 that filled substantially all of the spaces inside casing 24 and around tubes 20 at a rate of 5.5 cubic feet per minute. Inlet and exit temperatures were monitored for gas mixture 36 through catalyst 16 and water through tubes 20 and annular passageway 14a as well as flow rates for each.

Approximately 22% of the stored chemical-energy from the hydrogen was transferred to the stream of water 54 during this steady flow in an open-circuit version of catalytic heater 10. This relatively low conversion of the chemical energy in the hydrogen into useful thermal energy was to be expected with an open-circuit version of catalytic heater 10 since a large percentage of the available energy was lost to the environment by way of the hot air stream of breathing gas 36 that was exhausted, or vented.

The energy wasted from the vented gas in the open-circuit version is reduced considerably by operating the gas stream in a closed, or semi-closed arrangement of catalytic heater 10 as shown in FIG. 1. Gas 36 is not vented through feeder line 40, but instead injector valve 37 is switched to feed, or recycle the hot gas stream from outlet 34b back through the multi-tube heat exchanger 18 after another small percentage of "make-up" hydrogen 32 is injected into gas circuit 34 via injector valve 31.

Hydrogen catalytic heater 10 can be used in an open, closed or semi-closed configuration to support surface tethered diving applications or autonomous, self-contained missions with free-swimming divers or within wet or dry underwater vehicles. Water temperatures can be easily adjusted when using this heater 10 by regulating the percentage of hydrogen 32 injected into bed of catalyst 16. Catalytic heater 10 can be used either as the primary active heating source or as a backup heating system in the event failure occurs to the primary heat source.

A wide range of catalysts 16 can be used to initiate the reaction in the bed of catalyst 16. Catalysts 16 all have a key component consisting of a precious metal such as platinum or palladium deposited on a support matrix such as carbon or alumina. Other suitable catalysts will suggest themselves in light of the teachings set forth herein.

Having the teachings of this invention in mind, modifications and alternate embodiments of this invention may be fabricated to have a wide variety of applications in other systems. For examples, in accordance with this invention, catalytic heater 10 could have different shapes, the tubing arrangement of multi-tube heat exchanger 18 could have different designs to transfer heat from different arrangements of catalyst 16 to provide suitable levels of heated liquid for undersea, dry-land and space applications, as needed without departing from the scope of this invention.

The disclosed components and their arrangements as disclosed herein all contribute to the novel features of this invention. Catalytic heater 10 of this invention provides a reliable and cost-effective means to generate heat that sustains a variety of operations in demanding applications. Therefore, catalytic heater 10 as disclosed herein is not to be construed as limiting, but rather, is intended to be demonstrative of this inventive concept.

It will be understood that many additional changes in the details, materials, steps and arrangement of parts, which have been herein described and illustrated in order to explain the nature of the invention, may be made by those skilled in the art within the principle and scope of the invention as expressed in the appended claims.

We claim:

1. A catalytic heater and diving suit to pass heated liquid therebetween comprising:
    a source of hydrogen;
    a source of oxygen;
    a gas circuit having a pair of valves, each valve being coupled to a separate one of said sources to mix said hydrogen and oxygen together;
    a catalyst coupled to said gas circuit to react with said mixed hydrogen and oxygen to produce heat; and
    a multi-tube heat exchanger coupled to exchange liquid with said diving suit and to pass said liquid therethrough, said multi-tube heat exchanger having said catalyst disposed therein to transfer said heat to said liquid in said multi-tube heat exchanger to create heated liquid for said diving suit.

2. The catalytic heater and diving suit according to claim 1 further comprising:
    a housing jacket closed at opposite ends by cap members to define a chamber containing said catalyst and multi-tube heat exchanger therein, said cap members having fittings to pass said liquid through said multi-tube heat exchanger, said gas circuit flowing said mixed hydrogen and oxygen to said catalyst in said multi-tube heat exchanger.

3. The catalytic heater and diving suit according to claim 2 wherein said multi-tube heat exchanger includes a plurality of tubes, a shell-shaped casing, and a pair of disc-shaped end members, said tubes and said casing being secured at opposite ends to said end members and extending there between, and said casing being disposed radially outwardly from said tubes to define sealed spaces around said tubes and inside said shell and end members.

4. The catalytic heater and diving suit according to claim 3 wherein said housing and said shell define an annular passageway therebetween to pass some of said liquid there through during heating thereof, and said tubes pass some of said liquid there through during heating thereof.

5. The catalytic heater and diving suit according to claim 4 wherein said catalyst is disposed in said spaces around said tubes inside said casing and said end members.

6. The catalytic heater and diving suit according to claim 5 further comprising:
    a hose loop connected to said multi-tube heat exchanger and said diving suit; and
    a pumping unit coupled to said hose loop to circulate said liquid therebetween.

7. The catalytic heater and diving suit according to claim 6 wherein said source of oxygen includes other gases.

8. The catalytic heater and diving suit according to claim 7 wherein said gas circuit has opposite ends coupled to extend through said housing and said casing at opposite ends to vent said mixed hydrogen and oxygen to said catalyst in a semi-closed gas loop circuit.

9. The catalytic heater and diving suit according to claim 8 wherein said hydrogen is about one percent of said oxygen and said other gases, and said liquid is water.

10. The catalytic heater and diving suit according to claim 9 wherein said catalyst is comprised of 0.8% palladium deposited on extruded carbon pellets.

11. The catalytic heater and diving suit according to claim 10 wherein said valves coupled to said source of oxygen and other gases and said source of hydrogen are actuated to create elevated pressures in said gas circuit and said catalyst to increase the production of heat in said catalyst.

12. The catalytic heater and diving suit according to claim 10 wherein said valves are coupled to a source of air and said source of hydrogen, said valves are actuated to increase the flow rate of air and hydrogen to increase production of heat in said catalyst and are actuated to decrease the flow rate of air and hydrogen to decrease production of heat in said catalyst.

13. The catalytic heater and diving suit according to claim 10 wherein said valves are coupled to a source of air and said source of hydrogen, said valves are actuated to increase the percentage of hydrogen with respect to said air to increase the production of heat in said catalyst and are actuated to decrease the percentage of hydrogen with respect to said air to decrease the production of heat in said catalyst.

14. The catalytic heater and diving suit according to claim 7 wherein said gas circuit has one end coupled to extend through one end of said housing and said casing at one end to vent said mixed hydrogen and oxygen to said catalyst in an open circuit.

15. A method of heating liquid for a diving suit comprising the steps of:

coupling sources of hydrogen and oxygen to a gas circuit;

mixing said hydrogen and oxygen together in said gas circuit;

feeding said mixed hydrogen and oxygen to a catalyst inside a heat exchanger;

reacting said mixed hydrogen and oxygen with said catalyst;

producing heat by said reacting;

circulating liquid through said heat exchanger;

heating said liquid with said heat; and coupling said heated liquid to a diving suit.

* * * * *